(12) United States Patent
Demharter

(10) Patent No.: US 10,674,990 B2
(45) Date of Patent: Jun. 9, 2020

(54) TRANSMITTING SIGNALS IN A MEDICAL IMAGING SYSTEM

(71) Applicant: Nikolaus Demharter, Dormitz (DE)

(72) Inventor: Nikolaus Demharter, Dormitz (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/212,149

(22) Filed: Dec. 6, 2018

(65) Prior Publication Data
US 2019/0110770 A1 Apr. 18, 2019

Related U.S. Application Data

(63) Continuation of application No. 14/975,776, filed on Dec. 19, 2015, now Pat. No. 10,178,983.

(30) Foreign Application Priority Data

Dec. 19, 2014 (DE) .......................... 10 2014 226 686

(51) Int. Cl.
*A61B 6/00* (2006.01)
*G01R 33/36* (2006.01)
*A61B 6/03* (2006.01)

(52) U.S. Cl.
CPC .......... *A61B 6/563* (2013.01); *G01R 33/3692* (2013.01); *A61B 6/032* (2013.01); *A61B 6/037* (2013.01); *G01R 33/3621* (2013.01)

(58) Field of Classification Search
CPC ......... A61B 6/563; A61B 6/032; A61B 6/037; G01R 33/3621; G01R 33/3692; G01R 33/34; G01R 33/3415; G01R 33/341; G01R 33/288; G01R 33/543; G01G 19/445

USPC ......................................................... 324/322
See application file for complete search history.

(56) References Cited

U.S. PATENT DOCUMENTS

| 6,726,626 B1 * | 4/2004 | Hossack ............... B06B 1/0292 331/116 R |
| 8,917,093 B2 * | 12/2014 | Schmidt ............... G01R 33/341 324/322 |
| 9,316,708 B2 * | 4/2016 | Eberler ................ A61B 5/0555 |
| 10,178,983 B2 * | 1/2019 | Demharter ............. A61B 6/563 |
| 2005/0127914 A1 | 6/2005 | Eberler et al. |
| 2013/0057284 A1 | 3/2013 | Schmidt |
| 2013/0307772 A1 * | 11/2013 | Wu ....................... G06F 3/0304 345/158 |

(Continued)

FOREIGN PATENT DOCUMENTS

| DE | 10314215 B4 | 11/2006 |
| DE | 102011004913 A1 | 9/2012 |

(Continued)

OTHER PUBLICATIONS

German Office Action for related German Application No. 10 2014 226 686.6, dated Oct. 20, 2015, with English Translation, considered in U.S. Appl. No. 14/975,776.

*Primary Examiner* — Afsar M Qureshi
(74) *Attorney, Agent, or Firm* — Lempia Summerfield Katz LLC

(57) ABSTRACT

Apparatuses and a method are provided for transmitting signals in a medical imaging system. The method includes transmitting signals wirelessly between at least one receive facility and a facility of the imaging system via a radio network.

20 Claims, 4 Drawing Sheets

(56) References Cited

U.S. PATENT DOCUMENTS

2014/0361769 A1\* 12/2014 Hardie ............... G01R 33/3692
                                                            324/307
2015/0335243 A1\* 11/2015 Assmann ................. A61B 7/04
                                                            600/301
2016/0054413 A1\*  2/2016 Demharter ......... G01R 33/3607
                                                            324/309

FOREIGN PATENT DOCUMENTS

| DE | 102013210381 B3 | 5/2014 |
| DE | 102014216402 A1 | 2/2016 |
| WO | WO-2013153801 A1 \* | 10/2013 |
| WO | WO-2014177971 A1 \* | 11/2014 |
| WO | WO2014177971 A1 | 11/2014 |

\* cited by examiner

TRANSMITTING SIGNALS IN A MEDICAL IMAGING SYSTEM

CROSS-REFERENCE TO RELATED APPLICATIONS

This application is a continuation of U.S. patent application Ser. No. 14/975,776, filed Dec. 19, 2015, now U.S. patent. No. 10,178,983 B2, issued on Jan. 15, 2019, which claims the benefit of German Patent Application No. DE 10 2014 226 686.6, filed on Dec. 19, 2014. These documents are hereby incorporated by reference in their entirety.

TECHNICAL FIELD

The present embodiments relate to methods and apparatuses for transmitting signals in a medical imaging system.

BACKGROUND

Magnetic resonance devices (MRTs) and/or transmission methods are described, for example, in DE 103 14 215 B4, DE 10 2014 216 402, and DE 10 2013 210 381.6, which are hereby incorporated by reference in their entirety.

SUMMARY AND DESCRIPTION

The scope of the present invention is defined solely by the appended claims and is not affected to any degree by the statements within this summary. The present embodiments may obviate one or more of the drawbacks or limitations in the related art.

The present embodiments may obviate one or more of the drawbacks or limitations in the related art. For example, a transmission of signals in a medical imaging system (e.g., a magnetic resonance tomography system) is optimized.

DETAILED DESCRIPTION

Figure 4:
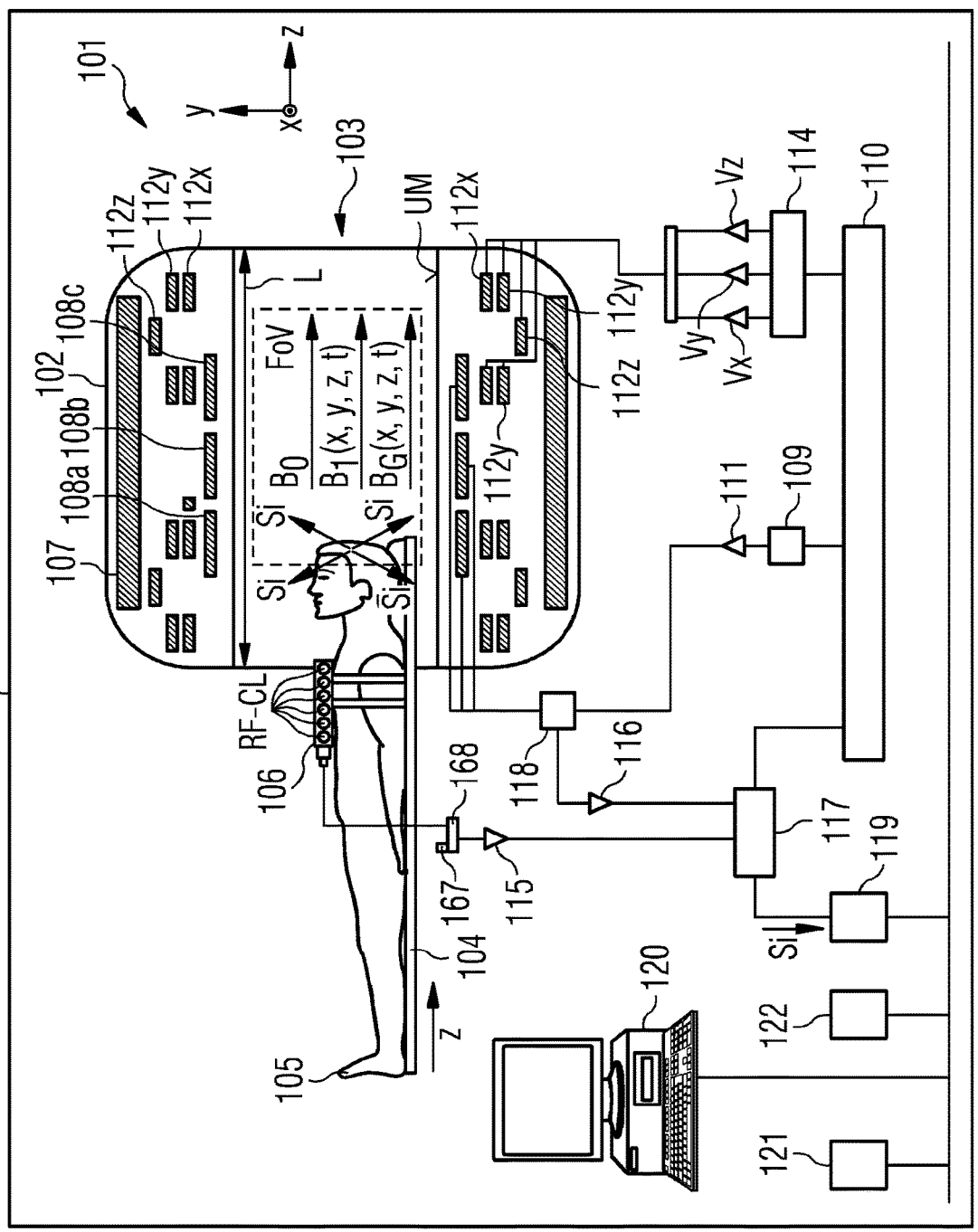
FIG. 4 depicts an embodiment of a MRT system.

FIG. 4 depicts an imaging magnetic resonance device MRT 101 (e.g., contained in a shielded room or Faraday cage F) including a hollow cylinder 102 having, for example, a tubular bore 103 into which a patient couch 104 bearing a body 105 (e.g., of an examination object such as a patient; with or without local coil arrangement 106) may be introduced in the direction of the arrow z so that images of the patient 105 may be generated by an imaging method. Disposed on the patient 105 is, for example, a local coil arrangement 106 that may be used in a local region (e.g., Field of View (FoV)) of the MRT to generate images of a subregion of the body 105 in the FoV. Signals of the local coil arrangement 106 may be evaluated (e.g., converted into images, stored or displayed) by an evaluation device (e.g., including elements 168, 115, 117, 119, 120, 121, etc.) of the MRT 101 that may be connected to the local coil arrangement 106 (e.g., via coaxial cable or wirelessly (element 167), etc.).

When a magnetic resonance device MRT 101 is used in order to examine a body 105 (e.g., an examination object or a patient) by magnetic resonance imaging, different magnetic fields that are coordinated with one another with precision in terms of temporal and spatial characteristics are radiated onto the body 105. A strong magnet (e.g., a cryomagnet 107) in a measurement chamber having, for example, a tunnel-shaped bore 103 generates a strong static main magnetic field B0 ranging, for example, from 0.2 Tesla to 3 Tesla or more. A body 105 that is to be examined, supported on a patient couch 104, is moved into a region of the main magnetic field B0 that is approximately homogeneous in the area of observation FoV. The nuclear spins of atomic nuclei of the body 105 are excited by magnetic radio-frequency excitation pulses B1(x, y, z, t) that are emitted via a radio-frequency antenna (and/or a local coil arrangement if necessary) that is depicted in greatly simplified form as a body coil 108 (e.g., a multipart coil 108a, 108b, 108c). Radio-frequency excitation pulses are generated, for example, by a pulse generation unit 109 that is controlled by a pulse sequence control unit 110. Following amplification by a radio-frequency amplifier 111, the pulses are directed to the radio-frequency antenna 108. The radio-frequency system shown is indicated only schematically. Often more than one pulse generation unit 109, more than one radio-frequency amplifier 111, and a plurality of radio-frequency antennas 108 a, b, c are used in a magnetic resonance device 101.

The magnetic resonance device 101 also has gradient coils 112x, 112y, 112z by which magnetic gradient fields are radiated in the course of a measurement in order to provoke selective layer excitation and for spatial encoding of the measurement signal. The gradient coils 112x, 112y, 112z are controlled by a gradient coil control unit 114 (and if appropriate, via amplifiers Vx, Vy, Vz) that, like the pulse generation unit 109, is connected to the pulse sequence control unit 110.

Signals emitted by the excited nuclear spins (e.g., of the atomic nuclei in the examination object) are received by the body coil 108 and/or at least one local coil arrangement 106, amplified by assigned radio-frequency preamplifiers 116, and further processed and digitized by a receive unit 117. The recorded measurement data is digitized and stored in the form of complex numeric values in a k-space matrix. An associated MR image may be reconstructed from the value-filled k-space matrix by a multidimensional Fourier transformation.

For a coil that may be operated in both transmit and receive mode (e.g., the body coil 108 or a local coil 106), correct signal forwarding is regulated by an upstream duplexer 118. From the measurement data, an image processing unit 119 generates an image that is displayed to a user via an operator console 120 and/or stored in a memory unit 121. A central computer unit 122 controls the individual system components.

In MR tomography as practiced today, images having a high signal-to-noise ratio (SNR) may be acquired by local coil arrangements (e.g., coils, local coils). These are antenna systems that are mounted in immediate proximity to (on (anterior) or under (posterior)), on, or in the body 105. In the course of an MR measurement, the excited nuclei induce a voltage in the individual antennas of the local coil. The voltage is then amplified by a low-noise preamplifier (e.g., LNA, preamp) and finally forwarded to the receive electronics. High-field systems (e.g., 1.5 T-12 T or more) are used to improve the signal-to-noise ratio, even with high-resolution images. Since more individual antennas may be connected to an MR receiving system than there are receivers present, a switching matrix (e.g., RCCS) is installed between receive antennas and receivers. The array routes the currently active receive channels (e.g., the channels currently lying in the field of view of the magnet) to the receivers present. This enables more coil elements to be connected than there are receivers available, since in the case of whole-body coverage, only the coils that are located in the FoV or in the homogeneity volume of the magnet may be read out.

The term local coil arrangement 106 may describe, for example, an antenna system that may include one antenna element or a plurality of antenna elements (e.g., coil elements) configured as an array coil. These individual antenna elements are embodied, for example as loop antennas (e.g., loops), butterfly coils, flex coils or saddle coils. A local coil arrangement includes, for example, coil elements, a preamplifier, further electronics (e.g., standing wave traps, etc.), a housing, supports, and in most cases a cable with plug-type connector by which the local coil arrangement is connected to the MRT system. A receiver 168 mounted on the MRT system side filters and digitizes a signal received, for example, wirelessly, etc. by a local coil 106 and passes the data to a digital signal processing device. The digital signal processing device may derive an image or a spectrum from the data acquired by a measurement and make the image or the spectrum available to the user, for example, for subsequent diagnosis by the user and/or for storage in a memory.

FIGS. 1-4 show some details of examples of embodiments.

Embodiments may be used as a replacement to cables and/or modules in an imaging (MRT) system by using a wireless LAN (e.g., WLAN with 60 GHz and/or 802.11 ad).

Figure 1:
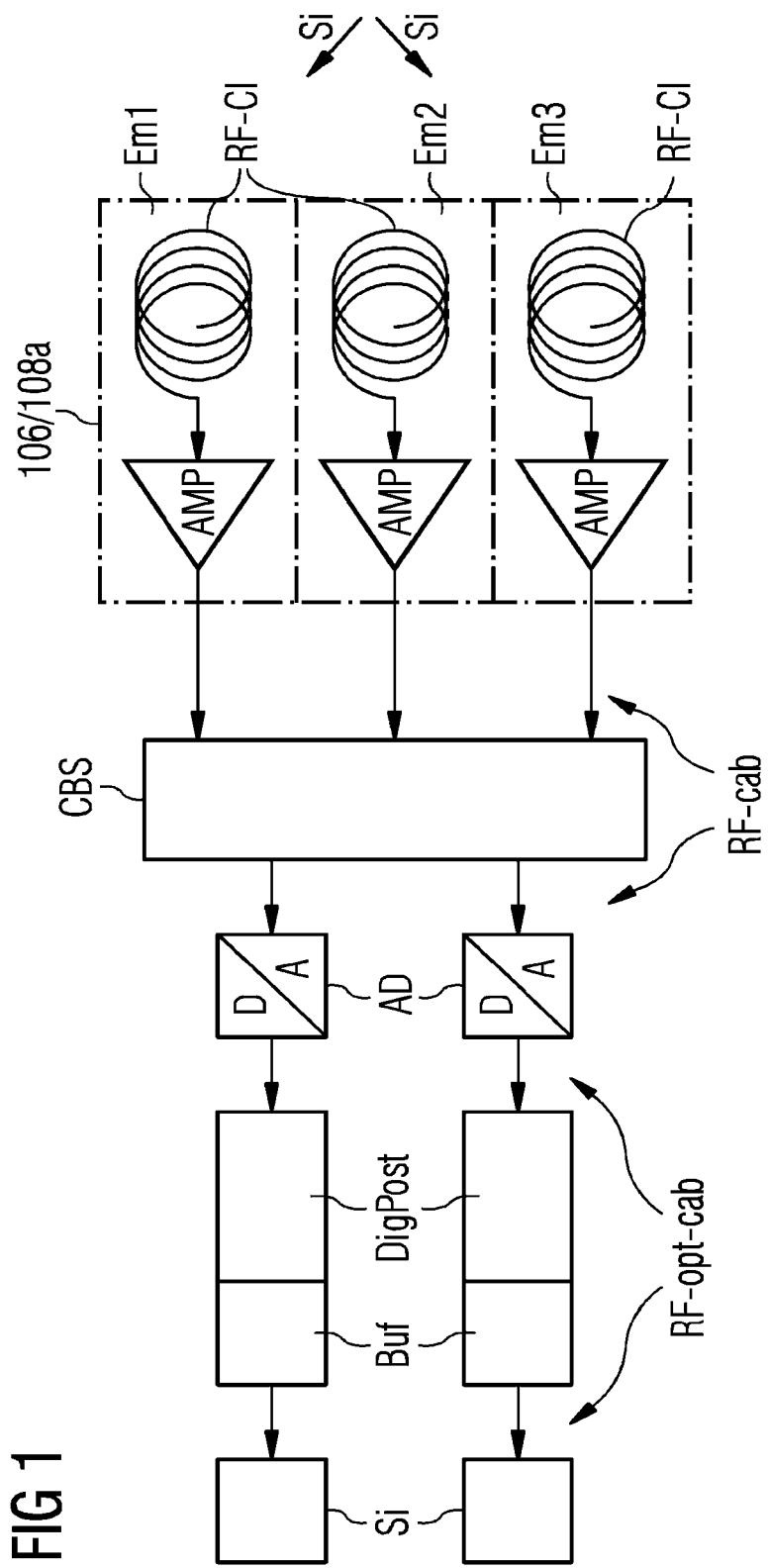
FIG. 1 depicts an embodiment of a transmission of signals in a MRT.

FIG. 1 depicts a schematic representation of a signal receive path of known MRT systems 101.

The signal receive path has parallel RF coils RF-CL (e.g., antennas or RF coils or transmit and receive coils) receiving one or more signals Si, in each case, one or more segments Em1, Em2, Em3 (e.g., in one or more local coils 106 and/or the MRT body coil) with, for example, in each case an amplifier AMP, a distributor CBS, A/D converter AD, and a digital post-processing DigPost (e.g., with buffer Buf) for generating post-processed signals Si.

For cost reasons, the number of A/D converters may be lower than the maximum number of usable coil segments and/or antennas RF-C1.

The connections between RF coils RF-CL and A/D converters establish a crossbar switch CBS (e.g., bridge network) that assigns the RF coils RF-CL used (and/or partial segments Em1, Em2, Em3 of a local coil 106), for example, depending on the position in the magnetic field and recording sequence to an A/D converter AD. Therefore, up to 204 coil elements RF-CL may be connected to, for example, 24 A/D converters AD.

The connections (like in FIG. 1, the electrical cable connections RF-Cab and optical cable connections RF-opt-cab) between the receive modules Em1, Em2, Em3 (e.g., each with at least one RF coil (antenna) RF-CL) via the crossbar switch CBS to an A/D converter AD may, on account of the plurality and the plug-in design of different local coils, may be complex.

Figure 2:
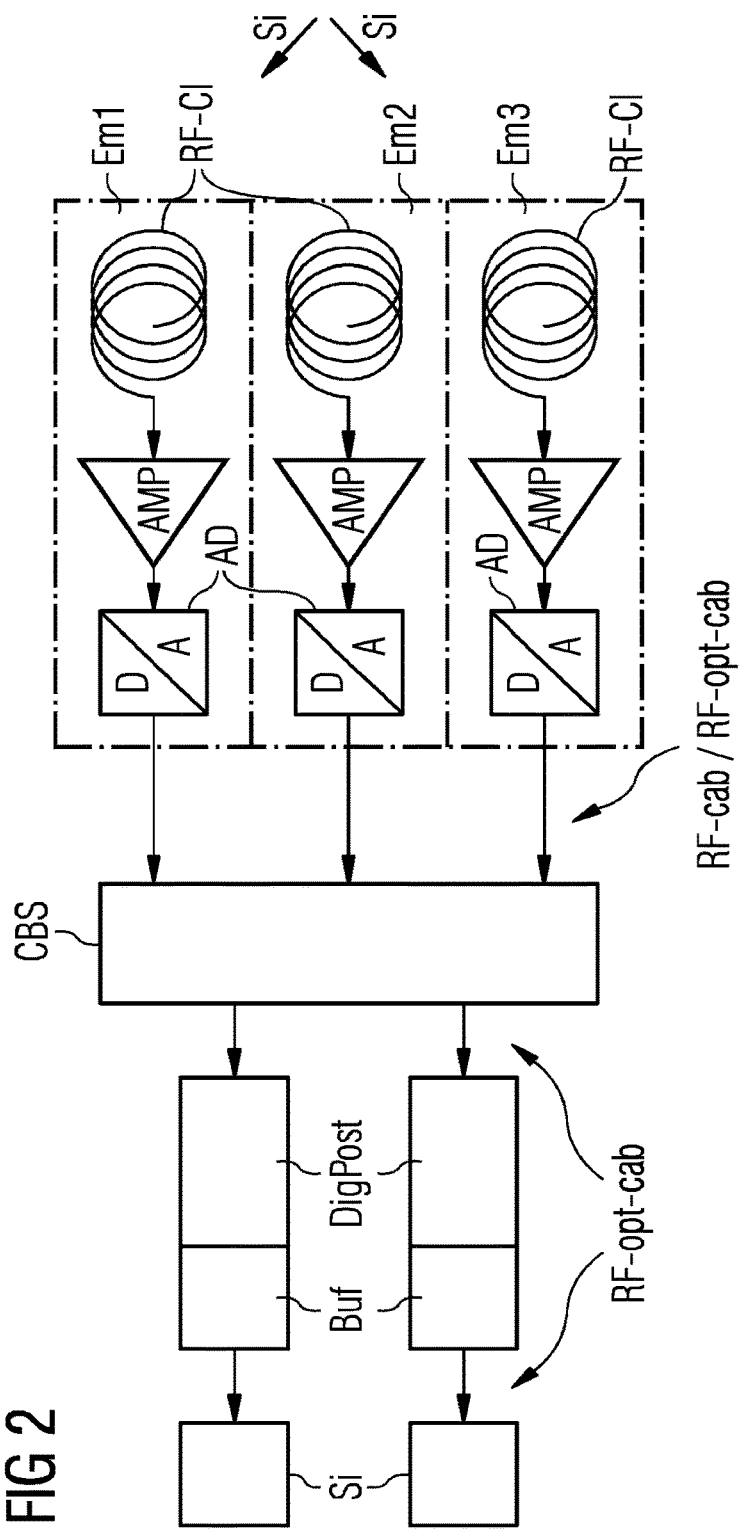
FIG. 2 depicts an embodiment of a transmission of signals in a MRT.

A displacement of the A-D converter AD into the at least one local coil 106 as in FIG. 2 may be advantageous in replacing expensive analog connections (like in FIG. 1, the electrical cable connections RF-Cab and/or optical cable connections RF-opt-cab) with possibly more cost-effective digital connections on electrical and/or optical cables (RF-Cab, RF-opt-cab).

Figure 3:
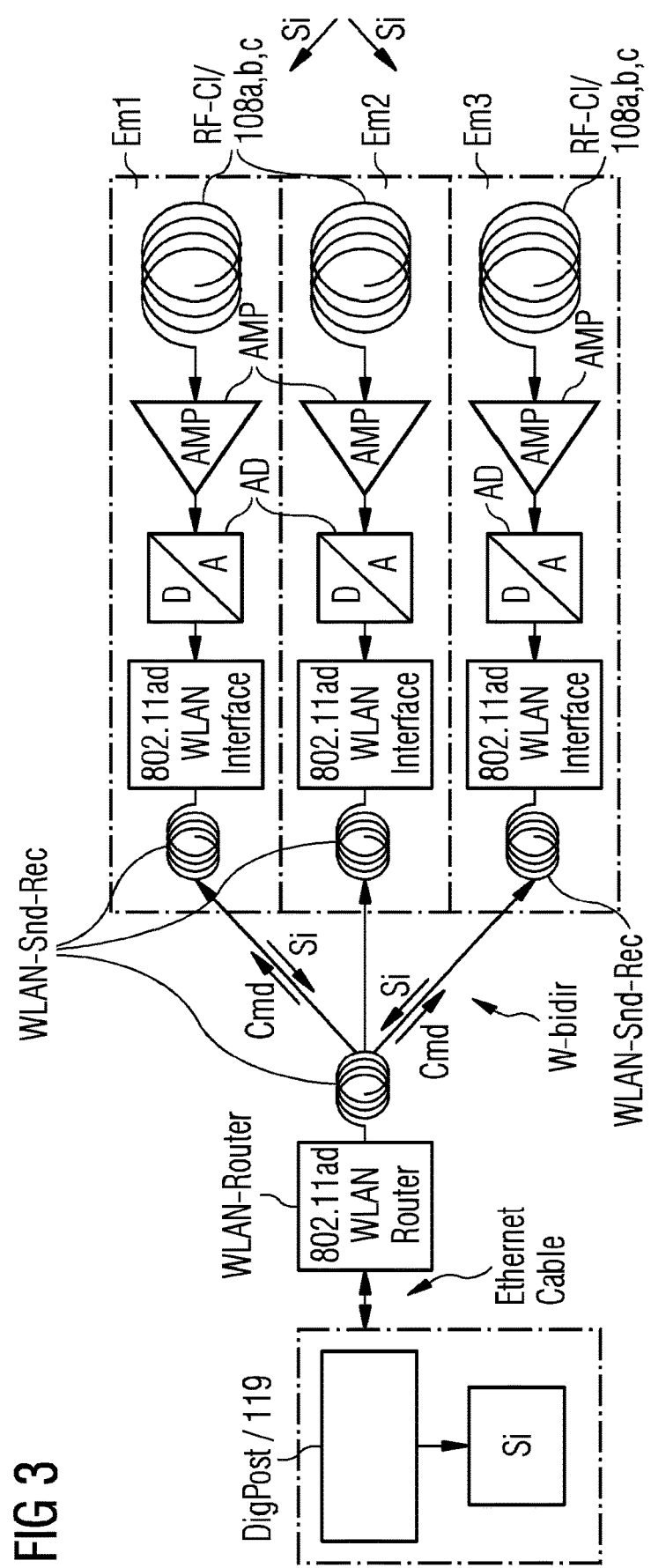
FIG. 3 depicts an embodiment of a WLAN transmission of signals in a MRT.

As shown in FIG. 3, according to embodiments (e.g., under the prerequisite of the measures described in the application DE 10 2014 216 402.8 to obtain the coherence of the MRT receive signals), the transmission of the digital signals Si (if necessary and/or Cmd) between receive modules Em1, Em2, Em3 (e.g., with in each case at least one RF coil RF-CL) and a facility (e.g., an evaluation facility 119 and/or a controller 110) of an imaging device (e.g., MRT 101) may be wireless (e.g., by WLAN (W-bidir); up to an Ethernet).

A wireless transmission according to embodiments may, depending on the scanning rate and A-D converter resolution, and, if necessary, compression or data reduction performed, require transmission bandwidths, for example, on the order of magnitude of 100 Mbit/second per coil segment. Such a transmission may take place, for example, by proprietary protocols and modulation schemes. An embodiment may use a standardized protocol that operates in a non-licensed radio band. This protocol may enable a simple (e.g., worldwide) radio license if the frequency bands are regulated by standard law. The radio standard according to 802.11ad allows this (e.g., in the 60 GHz band). For example, by using routers and radio modules already commercially available for other purposes, the development outlay may be reduced.

As shown in FIG. 3, a receive path may be provided with a WLAN (W-bidir) between the send-receive modules (WLAN router) on the part of the MRT 101 and one or more send-receive modules (WLAN-Snd-Rec) on the part of a local coil 106.

Any relatively expensive analog and digital previously known cable-based signal connections may be replaced (e.g., partially) by wireless (WLAN) connections. A previously used crossbar switch CBS may, for example, also then be unnecessary if it is possible to notify by way of the bidirectional connections W-bidir (e.g., radio connections) between a WLAN router and WLAN send-receive modules WLAN-Snd-Rec connected to the antennas RF-CL whether the antennas RF-CL are currently to be involved in the generation of the MRT image (e.g., then the antennas RF-CL are to send data and/or activate a sound) or not (e.g., then antennas RF-CL are not to send and if necessary, an energy-saving mode and/or a detuning are/is to be activated). Therefore not all coil segments RF-CL may be involved in the recording of an image at the same time. The overall bandwidth available may therefore be better distributed over the coil segments RF-CL involved.

A transmit bandwidth management system of this type allows the available overall bandwidth of, for example, up to 6.75 GBit/second to be used efficiently.

The local legal frequency bands may also be used in a country specific manner (e.g., channel management). In countries such as, for example, Australia, the use may be restricted to the only 2 channels permissible there.

On account of the high signal damping associated with the high transmit frequency, the 60 GHz band is suited to transmissions over short paths. The signal coverage is considerably shorter compared with the 5 GHz band. This may be considerably advantageous if, for example, disturbances by other radio subscribers in the 60 GHz band may as a result be ruled out, moreover the transmission takes place within the MR shielded chamber (e.g., Faraday cage).

The data transmission may take place during and after the receive time period of the AD converter (e.g., online and offline).

The data transmission itself may take place via (e.g., directed or undirected) free field transmission or guided waves (e.g., like or similar to in DE 10 2013 210 381.6, DE 10 2013 210 381.6).

The bidirectional (WLAN) radio transmission may also be used to tune or detune the individual coils or coil elements by corresponding signals (Cmd).

Moreover, further data (e.g., identification of the connected/usable coils) may be transmitted via the (WLAN) radio transmission.

A directed signal transmission may define whether a local coil 106 is disposed on the MR couch 105 and/or patient 104, or at another position in the room F.

The present embodiments may be applied or transferred analogously to CT devices (e.g., for the data transmission from a rotating gantry), x-ray devices (e.g., for data transmission from a detector to an image computer), a PET scanner (e.g., for data transmission of PET detections), and further medical devices.

Embodiments may also include the data transmission of the MRT transmit path.

Possible advantages may, for example, be provided as follows.

By using a standardized wireless WLAN protocol, with potentially comparatively low development costs, the manufacturing costs of the signal receive chain of MRT systems may possibly be reduced.

This may be achieved by reducing or avoiding expensive detachable RF cable connections, wires, and the crossbar switch.

A radio license process in the individual scanning areas may be facilitated compared with a proprietary radio solution.

In principle, the wireless transmission may also be transmitted by a proprietary radio protocol. However, the outlay involved in the development and licensing may be higher here. The wireless transmission may also take place by IEEE 802.11ac standard in the 5 GHz ISM band. The overall data rate compared with IEEE 802.11ad is nevertheless significantly restricted, and the probability of being influenced by other devices such as, for example, laptops or mobile telephones with 5 GHz LAN connections is considerably greater on account of the considerably broader signal coverage. With even older variants of the IEEE 802.11 standard, the data rate is restricted still further.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for transmitting signals in a medical imaging system, the method comprising:
    transmitting a first signal between at least one receiver and an imaging system device, the first signal being a command signal; and
    transmitting a second signal between the at least one receiver and the imaging system device,
    wherein transmitting the command signal and the second signal takes place wirelessly via a radio network within a B0 field generated by the medical imaging system, and
    wherein the B0 field has a field strength of greater than 0.2 Tesla.

2. The method of claim 1, wherein transmitting the command signal and the second signal comprises transmitting the command signal and the second signal wirelessly via a radio network in the form of a WLAN.

3. The method of claim 2, wherein the WLAN has an overall bandwidth available of 6.75 GBit/second, a frequency of 60 GHz, or a combination thereof.

4. The method of claim 2, wherein the WLAN uses local legal frequency bands by a channel management.

5. The method of claim 2, wherein the WLAN uses IEEE 802.11ac or IEEE 802.11ad.

6. The method of claim 1, wherein the medical imaging system comprises a magnetic resonance tomography system, and the at least one receiver comprises at least one antenna of a local coil.

7. The method of claim 1, wherein the medical imaging system comprises a computer tomography (CT) device, an x-ray device, or a PET scanner.

8. The method of claim 1, further comprising:
    receiving, by the at least one receiver, signals coming from a patient; and
    amplifying, analog-digital converting, or amplifying and analog-digital converting the received signals prior to sending the signal to an image processing unit of a magnetic resonance tomography system via a WLAN.

9. The method of claim 8, wherein transmitting the first and second signals takes place during, after, or during and after a receive time frame of an analog-digital (AD) converter.

10. The method of claim 1, wherein the radio network transmits signals bidirectionally between a local coil and an image processing unit.

11. The method of claim 1, wherein the radio network transmits signals from a controller to a local coil, the signals triggering the local coil to deactivate, detune, to send signals, to switch on an energy-saving mode on at least one antenna, receive modules of the local coil, or the at least one antenna and the receive modules, or any combination thereof.

12. The method of claim 1, wherein in a magnetic resonance tomography (MRT) transmit path of a magnetic resonance tomography system, the radio network transmits signals from a controller to a local coil, the signals triggering the local coil to send RF signals defined by the signals.

13. The method of claim 1, wherein an overall bandwidth of the radio network available at a time instant for transmission of signals is less than all coil segments, antennas, or coil segments and antennas of a local coil.

14. The method of claim 1, wherein transmitting the first and second signal takes place through the radio network within a shielded chamber of a magnetic resonance tomography system.

15. The method of claim 1, wherein transmitting the first and second signals is via directed or undirected free field transmission or guided waves.

16. The method of claim 1, wherein the command signal contains an identification of connected antennas, usable antennas, or connected and useable antennas.

17. The method of claim 1, wherein the command signal and the second signal contain data that specifies whether a local coil is disposed on an MRT couch, on a patient, on the MRT couch and on the patient, or at another location.

18. The method of claim 1, further comprising:
   detuning a local coil or an element of the local coil based on the command signal.

19. A medical imaging system comprising:
   a local coil; and
   an imaging processor configured to:
      transmit a command signal to the local coil wirelessly via a radio network and within a B0 field generated by the medical imaging system; and
      receive a signal from the local coil wirelessly via the radio network within the B0 field,
   wherein the B0 field has a field strength of greater than 0.2 Tesla.

20. The medical imaging system of claim 19, wherein the radio network is a WLAN.

\* \* \* \* \*